US011859750B2

(12) United States Patent
Iannone

(10) Patent No.: US 11,859,750 B2
(45) Date of Patent: Jan. 2, 2024

(54) MED-GAS PANEL CONNECTORS FOR RECONFIGURABLE WALLS

(71) Applicant: DIRTT Environmental Solutions Inc., Salt Lake City, UT (US)

(72) Inventor: Michael W. Iannone, Seattle, WA (US)

(73) Assignee: DIRTT ENVIRONMENTAL SOLUTIONS LTD., Calgary (CA)

( * ) Notice: Subject to any disclaimer, the term of this patent is extended or adjusted under 35 U.S.C. 154(b) by 323 days.

(21) Appl. No.: 16/646,021

(22) PCT Filed: Mar. 15, 2019

(86) PCT No.: PCT/US2019/022604
§ 371 (c)(1),
(2) Date: Mar. 10, 2020

(87) PCT Pub. No.: WO2019/178556
PCT Pub. Date: Sep. 19, 2019

(65) Prior Publication Data
US 2020/0271244 A1 Aug. 27, 2020

Related U.S. Application Data

(60) Provisional application No. 62/644,192, filed on Mar. 16, 2018.

(51) Int. Cl.
*F16L 5/10* (2006.01)
*A61G 12/00* (2006.01)
(Continued)

(52) U.S. Cl.
CPC .............. *F16L 5/10* (2013.01); *A61G 12/004* (2013.01); *A61G 12/005* (2013.01);
(Continued)

(58) Field of Classification Search
CPC ....... F16L 5/10; A61G 12/004; A61G 12/005; E04B 2/7407; E04B 2002/7488; E04C 2/46; E04C 2/526; E04H 3/08; A61M 16/0816
See application file for complete search history.

(56) References Cited

U.S. PATENT DOCUMENTS 3,462,892 A * 8/1969 Meyer ..................... E04C 2/521
52/28
5,562,121 A 10/1996 Hodges et al.
(Continued)

OTHER PUBLICATIONS

International Search Report and Written Opinion dated Jun. 10, 2019 from International Patent Application No. PCT/US2019/022604 filed Mar. 15, 2019.

*Primary Examiner* — Babajide A Demuren
(74) *Attorney, Agent, or Firm* — Workman Nydegger

(57) ABSTRACT

A medical-gas panel connector system includes a frame assembly. The frame assembly includes a horizontal frame member, a vertical frame member connected to the horizontal frame member, and a ceiling integration assembly. The medical-gas panel connector system also includes a medical-gas outlet removably secured to at least one of the horizontal frame member and the vertical frame member via a bracket. In addition, a manifold is removably secured to the ceiling integration assembly, the manifold being at least partially disposed inside the medical-gas panel connector system, and a flexible gas line connects the manifold to the medical-gas outlet. The medical-gas panel connector can be reconfigured and rearranged within a modular wall system.

18 Claims, 6 Drawing Sheets

(51) Int. Cl.
    *E04B 2/74*         (2006.01)
    *E04B 2/00*         (2006.01)
    *E04C 2/52*         (2006.01)
    *E04H 3/08*         (2006.01)

(52) U.S. Cl.
    CPC .............. *E04B 2/7407* (2013.01); *E04C 2/46* (2013.01); *E04C 2/526* (2013.01); *E04H 3/08* (2013.01)

(56) References Cited

U.S. PATENT DOCUMENTS

| | | | |
|---|---|---|---|
| 5,890,326 | A | 4/1999 | Gallant et al. |
| 6,953,498 | B2 | 10/2005 | Walker et al. |
| 7,152,604 | B2 | 12/2006 | Hickle et al. |
| 7,878,809 | B2 * | 2/2011 | Miller .................... G09B 23/28 52/29 |
| 8,522,488 | B1 * | 9/2013 | Newkirk .............. A61G 12/005 52/387 |
| 9,237,979 | B2 * | 1/2016 | Carnell ................ A61G 12/005 |
| 2008/0104901 | A1 * | 5/2008 | Olvera .................... E04C 2/521 52/173.1 |
| 2012/0258655 | A1 * | 10/2012 | Carnell ..................... E04H 3/08 454/284 |
| 2015/0075025 | A1 | 3/2015 | Newkirk et al. |

\* cited by examiner

MED-GAS PANEL CONNECTORS FOR RECONFIGURABLE WALLS

CROSS-REFERENCE TO RELATED APPLICATIONS

This application claims priority to and the benefit of U.S. Provisional Application Ser. No. 62/644,192 entitled "Med-Gas Panel Connectors for Reconfigurable Walls", filed on Mar. 16, 2018, the entire content of which is incorporated by reference herein in its entirety.

BACKGROUND OF THE INVENTION

1. The Field of the Invention

Embodiments of the present invention generally relate to modular wall systems for use in the healthcare industry. In particular, embodiments of the present invention relate to medical-gas panels and connectors for reconfigurable walls.

2. The Relevant Technology

Hospitals and other medical facilities commonly use headwalls in patient rooms. Headwalls provide medical gas outlets and connections for hoses to carry medical gases into a patient room for delivery to the patient or various medical systems and instruments. Outlets in headwalls are typically connected to central hospital gas supplies via copper pipes routed through the ceiling plenums and walls of the hospital. Typically, a plumber or other construction worker needs to braze or otherwise weld the copper pipes to lines within the headwall as well as a central gas line manifold residing inside the headwall of the patient room. These systems require pre-testing and/or certification before use and are/can be difficult to reconfigure or move.

Thus, current med-gas panel connectors and systems lack design flexibility. For example, reconfiguration of the headwall may require a plumber to totally deconstruct and reinstall the system. Flexibility of current headwall systems is therefore limited, and reconfiguration is expensive, time consuming, and complicated. In addition, reconfigurable wall systems currently lack features that provide med-gas panel connectors and systems that comply with industry regulations of gas delivery systems.

Accordingly, there are a number of disadvantages in headwalls and medical gas systems that can be addressed.

SUMMARY OF THE INVENTION

Embodiments of the present invention provide systems, methods and apparatus for implementing medical-gas (or, "med-gas") panel connectors in reconfigurable wall systems. For example, in one embodiment, a med-gas panel connector system includes a frame assembly. The frame assembly includes a horizontal frame member, a vertical frame member connected to the horizontal frame member, and a ceiling integration assembly. The med-gas panel connector system also includes a medical-gas outlet removably secured to at least one of the horizontal frame member and the vertical frame member via a bracket. In addition, a manifold is removably secured to the ceiling integration assembly, the manifold being at least partially disposed inside the medical-gas panel connector system, and a flexible gas line connects the manifold to the medical-gas outlet.

In one embodiment, a reconfigurable wall system includes two or more panels. The two or more panels include a medical-gas connector system. The medical-gas connector system includes a medical-gas outlet, a manifold, and a gas line. The medical-gas outlet has an inlet and a latch valve assembly, and the manifold has an inlet and an outlet. The gas line connects the outlet of the manifold to the inlet of the medical-gas outlet.

In one embodiment, a medical-gas panel connector system includes a ceiling integration assembly and a first manifold. The first manifold comprises an inlet extending through the ceiling integration assembly and an outlet that has a DISS adapter. The medical-gas panel connector system also includes a first medical-gas outlet having an inlet and a gas line that connects the inlet of the medical-gas outlet to the manifold.

Additional features and advantages of exemplary embodiments of the invention will be set forth in the description which follows, and in part will be obvious from the description, or may be learned by the practice of such exemplary embodiments. The features and advantages of such embodiments may be realized and obtained by means of the instruments and combinations particularly pointed out in the appended claims. These and other features will become more fully apparent from the following description and appended claims or may be learned by the practice of such exemplary embodiments as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments and/or embodiments thereof which are illustrated in the appended drawings. Understanding that these drawings depict only typical embodiments and/or embodiments of the invention and are not therefore to be considered to be limiting of its scope, the invention will be described and explained with additional specificity and detail through the use of the accompanying drawings in which.

DETAILED DESCRIPTION

Embodiments of the present invention provide systems, methods and apparatus for implementing medical-gas (or, "med-gas") panel connectors in reconfigurable wall systems. For example, in one embodiment, a med-gas panel connector system includes a frame assembly. The frame assembly includes a horizontal frame member, a vertical frame member connected to the horizontal frame member, and a ceiling integration assembly. The med-gas panel connector system also includes a medical-gas outlet removably secured to at least one of the horizontal frame member and the vertical frame member via a bracket. In addition, a manifold is removably secured to the ceiling integration assembly, the manifold being at least partially disposed inside the medical-gas panel connector system, and a flexible gas line connects the manifold to the medical-gas outlet.

As understood more fully from the specification and claims, the modular walls having med-gas panels of the present disclosure provide a number of important advantages in the art. For example, the med-gas panel connectors and systems of the present disclosure include internal frame members that incorporate a plurality of outlets, gas lines, and manifolds that are compliant with National Fire Protection Association (NFPA) 99 standards and regulations and can be easily installed and integrated into a pre-existing central gas system of a hospital or other medical facility.

The med-gas panel connectors can be incorporated into reconfigurable walls that are easy to replace and reconfigure depending on the specific needs of a patient room. The med-gas panel connectors of the present disclosure also simplify the plumbing required in typical med-gas headwall systems and use modular connections that do not require pre-testing or certification before use.

Figure 1A:
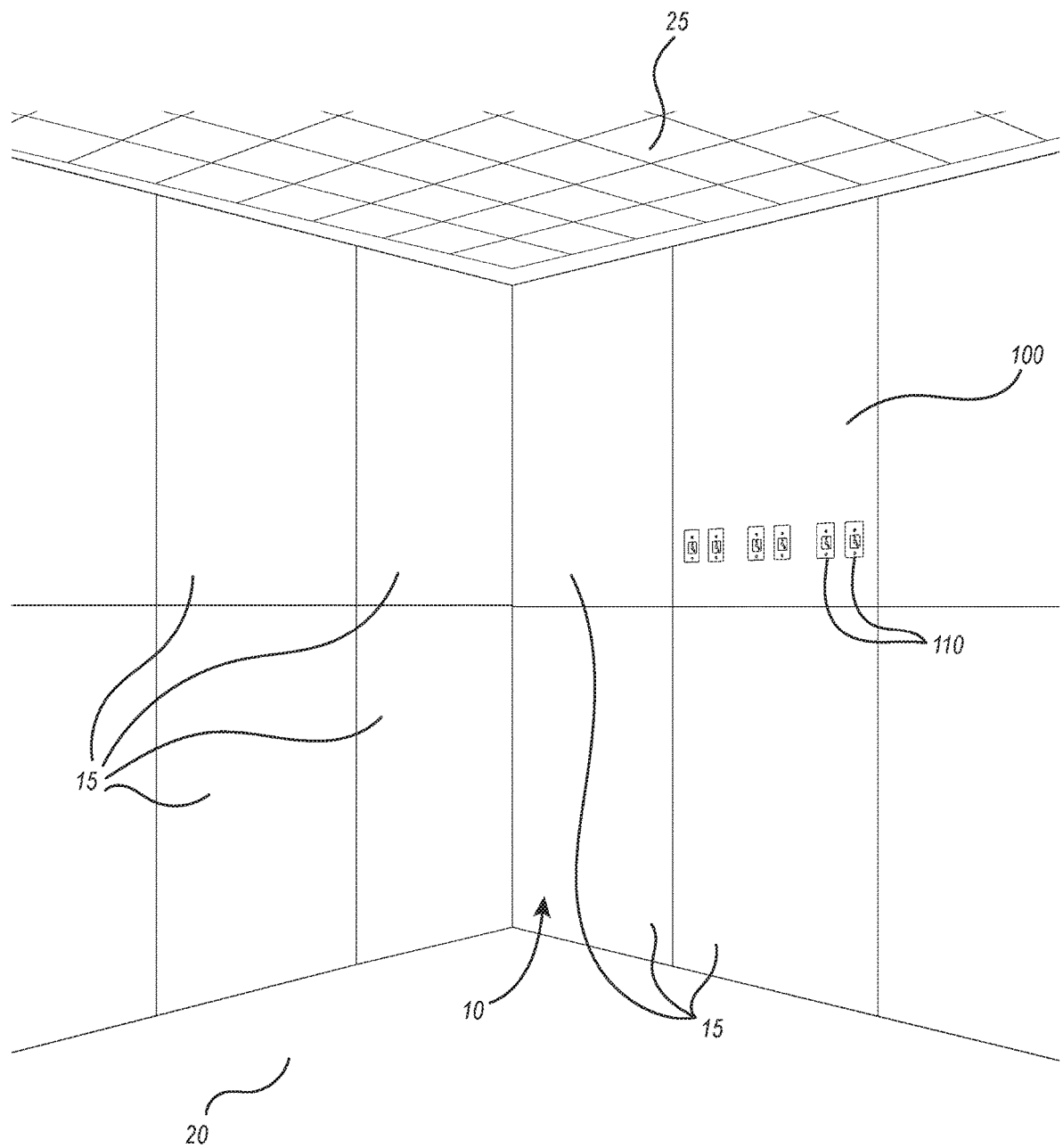
FIG. 1A illustrates a modular wall system including a med-gas panel connector system, according to an embodiment of the present disclosure.

Turning now to the figures, FIG. 1A illustrates a modular wall system 10 including a med-gas panel connector system 100. In at least one embodiment, the modular wall system 10 comprises a number of individual panels 15 removably secured together to form one or more walls within a patient room of a hospital. Modular wall systems 10 such as that illustrated in FIG. 1 are reconfigurable so that various spaces created by the modular wall system 10 can be formed as needed. These spaces, such as a patient room, operating room, or other rooms within a hospital, may thus be rearranged, customized, and reconfigured to meet the changing needs of the hospital.

For example, in at least one embodiment, the modular wall system 10 is configured to form a patient room. In such an embodiment, the modular wall system 10 extends from the floor 20 to the ceiling plenum 25 of the patient room to form a closed space in which one or more patients may reside. As noted above, in at least one embodiment, the modular wall system 10 includes a number of individual panels 15 removably secured together to form larger wall sections of the modular wall system 10.

The embodiment of the modular wall system 10 illustrated in FIG. 1A includes two wall portions removably secured together at a ninety-degree angle. However, in one or more other embodiments, any number of wall portions may be secured together at various angles to form various customized spaces. Also, one or more other embodiments of the modular wall system 10 may include more or less than the number and size of individual panels 15 shown in FIG. 1A.

Of particular note, at least a portion of the modular wall system 10 includes a med-gas panel connector system 100. At least one embodiment of a med-gas panel connector system 100 includes six med-gas outlets 110. The number of med-gas outlets 110 within a med-gas panel connector system 100 may vary in one or more other embodiments. Hospital patient rooms often require access to certain medical gases, such as oxygen, used for patients or medical devices within the room. Each med-gas outlet 110 provides an outlet to which a doctor or other medical professional can attach a hose or tube and route certain medical gases to the patient or medical device from the med-gas outlets 110.

In the illustrated embodiment of FIG. 1A, the modular wall system 10 includes a single med-gas panel connector system 100 that extends only partially between the ceiling plenum 25 and the floor 20. In at least one embodiment, the modular wall system 10 may comprise two or more med-gas panel connector systems 100. Also, in at least one embodiment, the size of the med-gas panel connector system 100 may be larger or smaller than that illustrated in FIG. 1A. For example, in at least one embodiment, the med-gas panel connector system 100 may form a panel of the modular wall system 10 that extends all the way from the ceiling plenum 25 to floor 20 of the patient room.

Various embodiments of the modular wall system 10 may comprise various sizes and number of individual panels 15 and med-gas panel connector systems 100 as needed for any particular room configuration. In addition, the placement of the med-gas panel connector system 100 may vary in one or more other embodiments. For example, in at least one embodiment, the med-gas panel connector system 100 is disposed on a lower section of the modular wall system 10.

Hospitals typically include central gas supplies and central gas lines to carry gases from the central gas supply through the walls, ceiling plenums, and floors of the hospital. The med-gas outlets 110 illustrated in FIG. 1A are connected to the central gas lines of the hospital through the med-gas panel connector system 100. Various components of the med-gas panel connector system 100, including the med-gas outlets 110 and other internal components (not shown in FIG. 1A) are modular and rearrangeable so that the modular wall system 10 can incorporate the med-gas panel connector system 100 at various positions within the modular wall system 10 and still connect to the central gas lines of the hospital with minimal effort and complication.

Figure 1B:
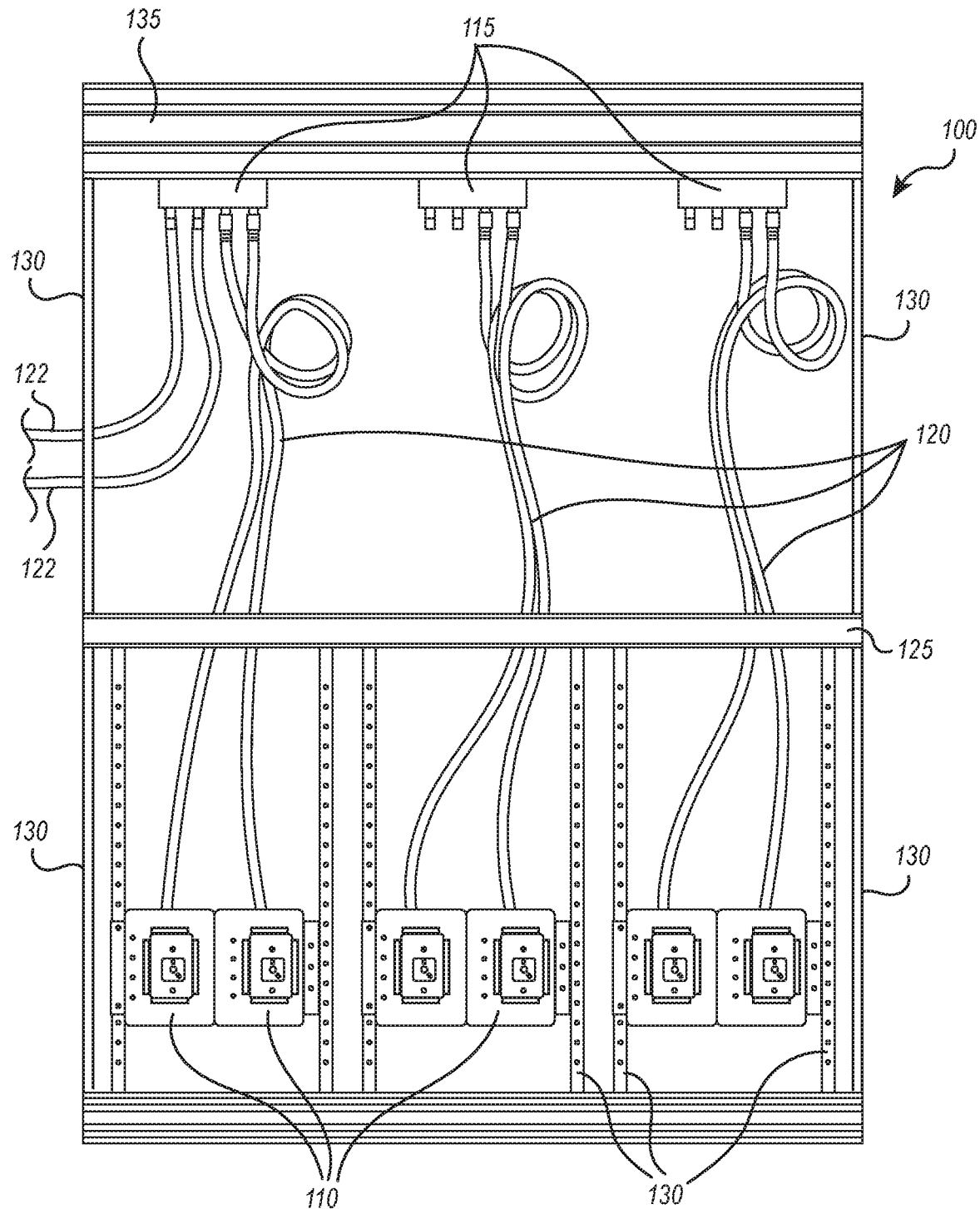
FIG. 1B illustrates a med-gas panel connector system for use in a modular wall system, according to an embodiment of the present disclosure.

Along these lines, FIG. 1B illustrates the med-gas panel connector system 100 shown in FIG. 1A with the outer panel or cover removed. As such, the internal components of the med-gas panel connector system 100 that allow the aforementioned design flexibility within the modular wall system 10 are shown.

In at least one embodiment, the med-gas panel connector system 100 includes one or more med-gas outlets 110, one or more manifolds 115, and one or more gas lines 120 connecting the one or more manifolds 115 to the one or more med-gas outlets 110. In addition, the med-gas panel connector system 100 includes one or more horizontal frame members 125 and one or more vertical frame members 130. In at least one embodiment, the horizontal frame members 125 and the vertical frame members 130 are elongate members.

Additionally, or alternatively, at least one embodiment includes gas lines 120 having Diameter Index Safety System (DISS) adapters at the ends thereof for connecting to the manifold 115. The gas lines 120 and/or manifolds 115 may also include non-interchangeable screw thread (NIST) connections at the med-gas outlet 110 to ensure proper installation with the correct gas lines 120.

The gas lines 120 may also include NIST connections at either end so as to ensure industry standards and to be compatible with the manifolds 115 and med-gas outlets 110 of the med-gas panel connector systems 100 described herein. In addition, the gas lines 120 may comprise flexible hosing that bends and/or flexes without cracking or breaking.

In at least one embodiment, the med-gas panel connector system 100 includes one or more horizontal frame members 125 and one or more vertical frame members 130. The horizontal 125 and vertical 130 frame members provide structure to the med-gas panel connector system 100 and attachment points for the med-gas outlets 110, manifolds 115, and gas lines 120.

In at least one embodiment, the horizontal frame members 125 and the vertical frame members 130 comprise elongate members having one or more holes disposed therethrough. At least one embodiment of the med-gas panel connector system 100 also includes a ceiling integration assembly 135. An assembler and/or installer of the med-gas panel connector system 100 may route the one or more gas lines 120 through the holes in the horizontal frame members 125 and/or vertical frame members 130 between the manifolds 115 and med-gas outlets 110. Additionally, or alternatively, the installer or assembler can route gas lines 120 around the frame members 125, 130.

As seen in FIG. 1B, in at least one embodiment, the gas lines 120 are longer than the distance between a given manifold 115 and corresponding med-gas outlet 110. The flexibility of the gas lines 120 allows for the extra slack to be curled or bent within the med-gas panel connector system 100. In addition, the flexibility and modularity of the system allows for gas lines 120 which do not need to be cut perfectly to length.

Instead, one or more standard chosen lengths of gas lines 120 may be employed so that an installer and/or assembler of the med-gas panel connector system 100 can use the same length of gas lines 120 to connect any one manifold 115 to any med-gas outlet 110, even if the distance between the manifold 115 and med-gas outlet 110 varies between systems. Again, the assembler and/or installer does not need to precisely measure and cut gas lines 120 to the exact length. This saves time and costs associated with installing embodiments of the med-gas panel connector systems 100 described herein.

In addition, at least one embodiment of the med-gas panel connector system 100 includes one or more gas lines 122 routed from the illustrated med-gas panel connector system 100 to adjacent systems or through adjacent panels 15 of the modular wall system 10 illustrated in FIG. 1A. Thus, one or more gas lines 122 may advantageously extend from the manifolds 115 of one med-gas panel connector system 100 to the med-gas outlet 110 of another panel or system. Thus, in at least one embodiment, one or more manifolds 115 secured within one med-gas panel connector system 100 may provide connections for med-gas outlets 110 of one or more other portions of the modular wall system 10.

As such, in one or more embodiments, the med-gas panel connector system 100 may include med-gas outlets 110 but no manifolds 115. In such an embodiment, the med-gas outlets 110 are connected to the manifold(s) 115 of a separate med-gas panel connector system 100 via gas lines 122 routed through one or more holes in corresponding vertical frame members 130 and/or horizontal frame members 125. Accordingly, in embodiments of modular wall systems 10 that include more than one med-gas panel connector system 100, an installer and/or assembler may rearrange and reconfigure the placement of various med-gas outlets 110 as needed or desired.

Furthermore, once an installer or assembler installs the med-gas connection system 100 and other reconfigurable wall panels 15, the end user can easily replace, remove, relocate, or reconfigure the med-gas connection system 100 without necessarily replumbing or welding gas line 120 connections within the med-gas panel connector system 100 or reconfigurable wall system 10.

As noted above, each embodiment of med-gas panel connector systems 100 described herein are easily installed the reconfigurable with other reconfigurable wall panels 15 to form customizable spaces, such as hospital patient rooms, operating rooms, and the like. In at least one embodiment, the ceiling integration assembly 135 is integrated into the existing ceiling plenum 25 of a hospital or other healthcare facility, as seen in FIG. 1A.

Figure 2:
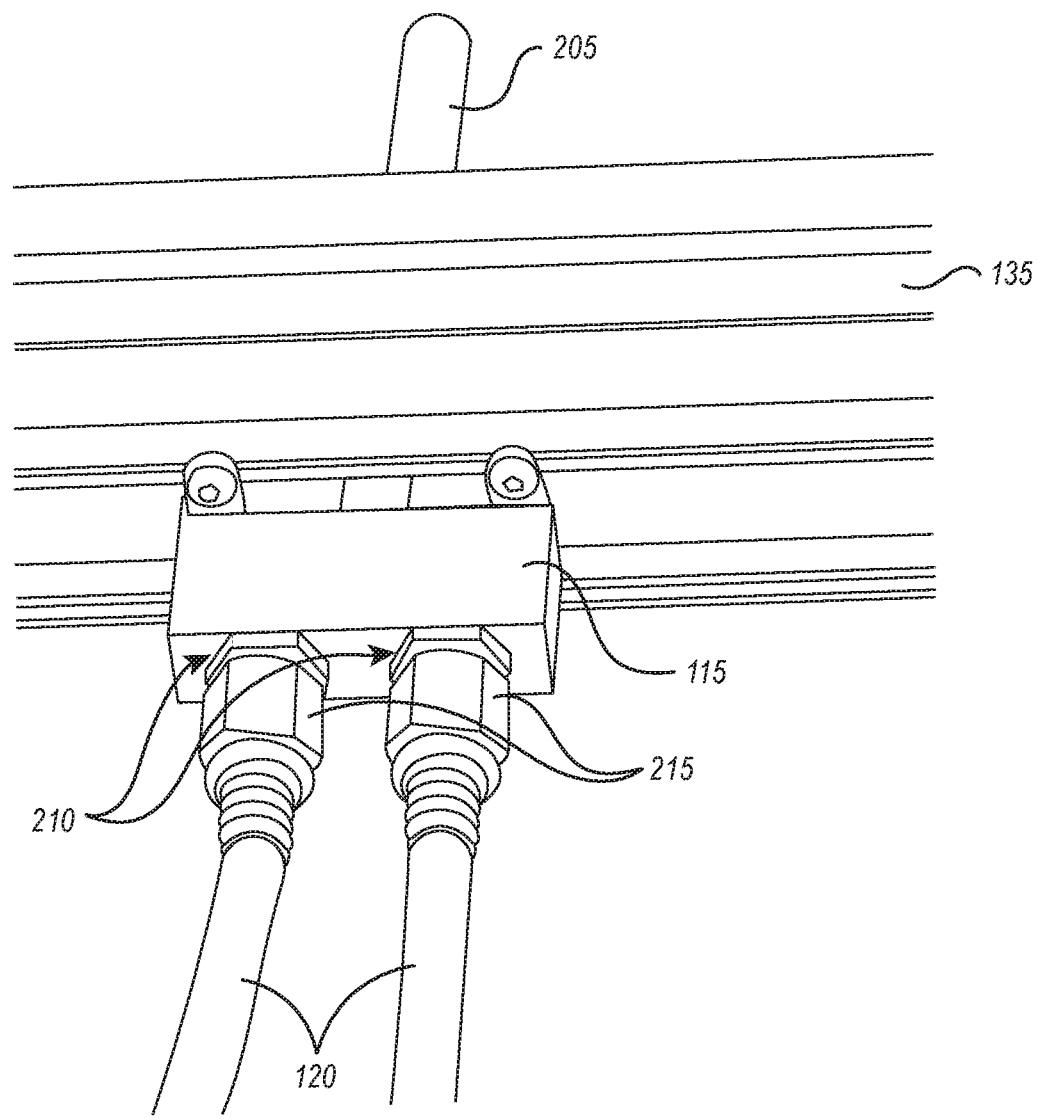
FIG. 2 illustrates a manifold for use in a med-gas panel connector system, according to an embodiment of the present disclosure.

Turning now to FIG. 2, as noted above, at least one embodiment of the med-gas panel connector system 100 includes one or more manifolds 115. FIG. 2 illustrates an embodiment of a manifold 115 according to the present disclosure. In at least one embodiment, the manifold 115 secures to the ceiling integration assembly 135 using bolts, screws, clips, or the like, or a combination thereof. In at least one embodiment, the manifold 115 is secured to the ceiling integration assembly 135 anywhere along the length of thereof. In this way, an installer or assembler can position the manifold 115 within the med-gas panel connector system 100 to correspond to the positions of the medical-gas outlets 110 or other frame members 125, 130.

In at least one embodiment, for example, the manifold 115 is positioned centrally along the length of the ceiling integration assembly 135. In at least one embodiment, the manifold 115 is positioned closer to the end of the ceiling integration assembly 135. In yet another embodiment, numerous manifolds 115 may be positioned at different locations along the length of the ceiling integration assembly 135. After installation, each manifold 115 secured to the ceiling integration assembly 135 may be rearranged or moved along the length of the ceiling integration assembly 135.

For example, after installing the manifold 115 shown in FIG. 2, an end user or installer can loosen or remove the screws, bolts, or other securement means noted above, slide or otherwise move the manifold 115 to a different location along the length of the ceiling integration assembly 135, and re-secure/re-tighten the securement means to secure the manifold 115 at a different location. In this way, in at least one embodiment, the manifold 115 is slidably or removably secured to the ceiling integration assembly 135.

In this way, the manifold 115 is easily reconfigurable and repositionable within the med-gas panel connector systems 100 described herein. Advantageously, as noted above, the gas lines 120 may include extra length, which allows the repositioning of the manifolds 115 and/or med-gas outlets 110 without removing the gas lines 120 from the manifolds 115 or the med-gas outlets 110. Thus, the gas lines 120 may advantageously remain secured to the manifolds 115 and/or med-gas outlets 110 as the manifolds 115 and/or med-gas outlets 110 are rearranged or reconfigured within the med-gas panel connector systems 100 described herein.

The manifold 115 includes a manifold inlet pipe 205, which extends from the top of the manifold 115 into the ceiling plenum 25 of the hospital or other health-care facility. In at least one embodiment, the manifold inlet pipe 205 connects to a central gas line or supply of the hospital to carry medical gas from the central gas line to the manifold 115.

In at least one embodiment, the manifold 115 includes one or more outlets 210 to deliver gases from the manifold 115 to the gas lines 120 of the med-gas connector system 100. In at least one embodiment, the outlets 210 are disposed at least partially within the medical-gas panel connector system 100. Each gas line 120 may connect to an outlet 210 of the manifold 115 via threaded nuts or other threaded connection mechanisms 215. As noted above, the outlets 210 of the manifold may include NIST connections to ensure that only compliant gas lines 120, which are appropriate for medical gas systems, can be connected to the outlets 210 of the manifold 115.

As a further safety precaution, in at least one embodiment, the one or more outlets 210 of the manifold 115 include a demand valve that only opens when the correct gas line 120 is connected to the outlet 210. In at least one embodiment, the gas line connection mechanism 215 includes the demand valve as well. In other embodiments, only the connection mechanism 215 includes a demand valve. In either case, one will appreciate that the demand valve ensures that the manifold 115 will not deliver medical gases to non-compliant and/or incorrectly placed gas lines 120. If, on the other hand, a manufacturer or assembler connects the correct gas line 120 to the outlet 210 of the manifold 115, the demand valve opens and allows medical gas to pass from the manifold inlet pipe 205, through the manifold 115, and into the gas line 120.

Figure 3A:
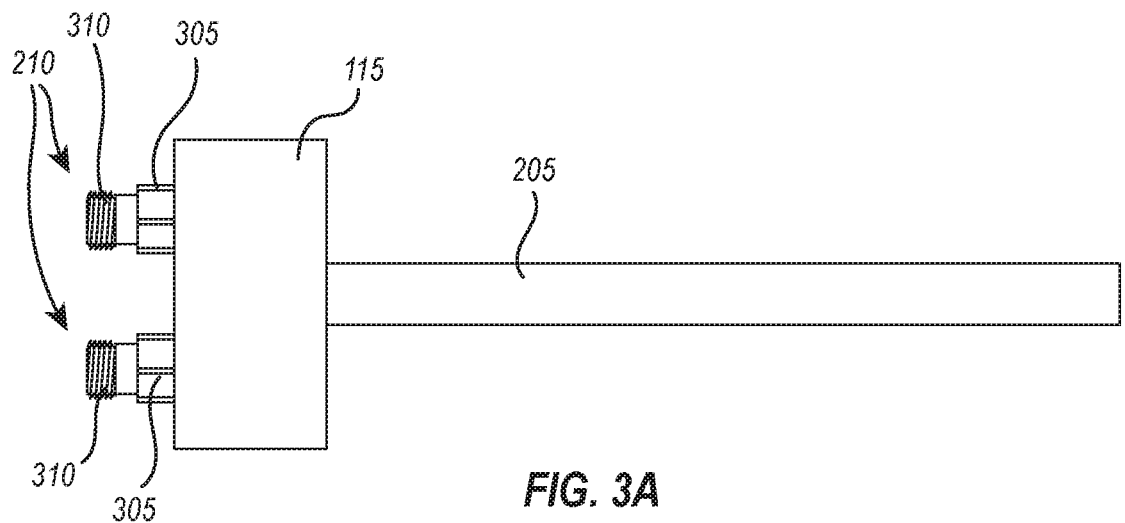
FIG. 3A illustrates a side view of a manifold, according to an embodiment of the present disclosure.
Figure 3B:
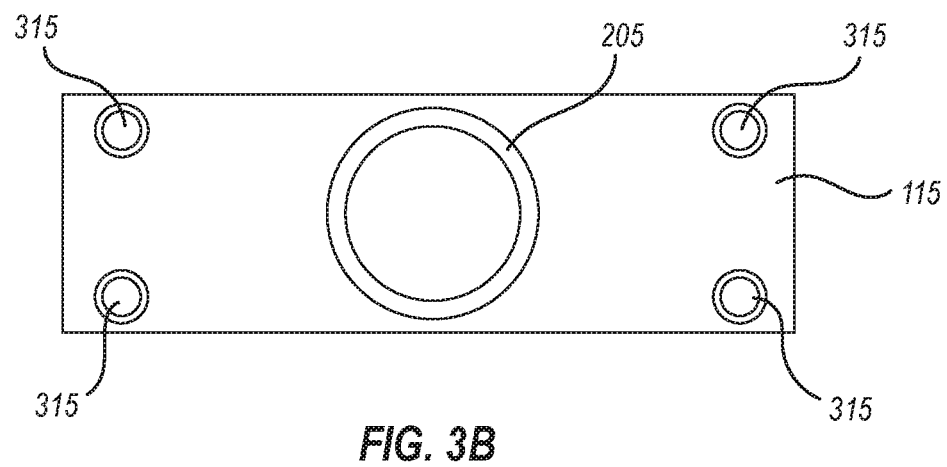
FIG. 3B illustrates a top view thereof.

FIGS. 3A and 3B illustrate an embodiment of a manifold 115 similar to the manifold 115 illustrated in FIG. 2. In particular, FIG. 3A illustrates a side view of an embodiment of the manifold 115. In at least the illustrated embodiment, the manifold 115 includes two outlets 210 extending opposite the manifold inlet pipe 205. In at least one embodiment, the outlets 210 each include a DISS adapter 305 and a threaded portion 310. Also, in at least one embodiment, the threaded portion 310 is customized to be unique, thus preventing incorrect connections of the industry standard gas lines 120 to the manifold 115, as noted above.

Each DISS adapter 305 may be separately installed on the outlets 210 of the manifold 115 depending on the need of the client. The DISS adapters 305 provide a connection that complies with industry regulations and is compatible with industry standard gas lines 120. Additionally, embodiments of manifolds 115 that include DISS adapters 305 do not need to be pre-tested or certified before use.

FIG. 3B illustrates a top view of the manifold 115 illustrated in FIG. 3A. FIG. 3B shows the manifold inlet pipe 205 connected to the top of the manifold 115 and threaded mounting holes 315. In at least one embodiment, the manifold 115 is secured to the ceiling integration assembly 135 of the modular wall system 105 via bolts extending through the threaded mounting holes 315, as shown in FIG. 2. As such, in at least one embodiment, the manifold 115 easily detaches and re-secures to various locations along the ceiling integration assembly 135 as needed. Also, in at least one embodiment, the gas lines 120 easily detach and re-attach to the various manifold outlets 210 as needed without brazing or welding.

Figure 4A:
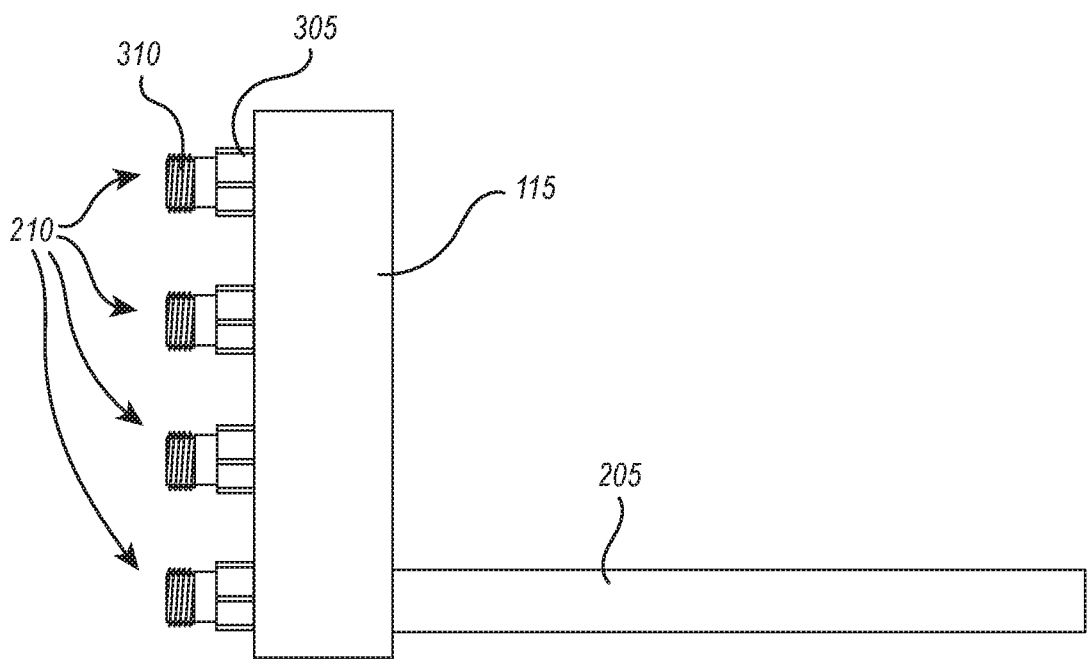
FIG. 4A illustrates a side view of a manifold for use in a med-gas panel connector system, according to the present disclosure.
Figure 4B:
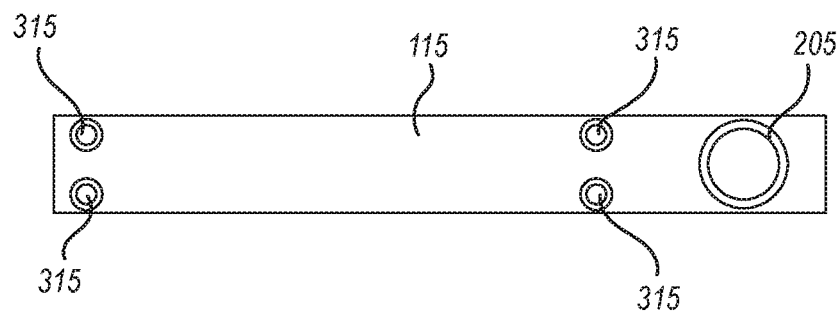
FIG. 4B illustrates a top view thereof.

At least one embodiment of the manifold 115, such as the manifold 115 of FIGS. 2-3B, include two outlets 210. At least one other embodiment may include more or less than two outlets 210. For example, FIGS. 4A and 4B illustrate a side view of an embodiment of a manifold 115 that includes four outlets 210. Again, in at least one embodiment, each outlet 210 includes a unique threaded portion 310 and a DISS adapter 305 similar to the manifold outlets 210 shown in FIG. 3A. FIG. 4B illustrates a top view of the manifold 115 of FIG. 4A, including four threaded mounting holes 315 and the manifold inlet pipe 205.

Various embodiments of the manifold 115 include any number or configuration of outlets 210. For example, at least one embodiment can include two or three outlets 210 of the same gas type. One or more other embodiments include four or more outlets 210. For example, other embodiments are configured with six outlets 210, seven outlets 210, eight outlets 210, nine outlets 210, or ten or more outlets 210.

Figure 5:
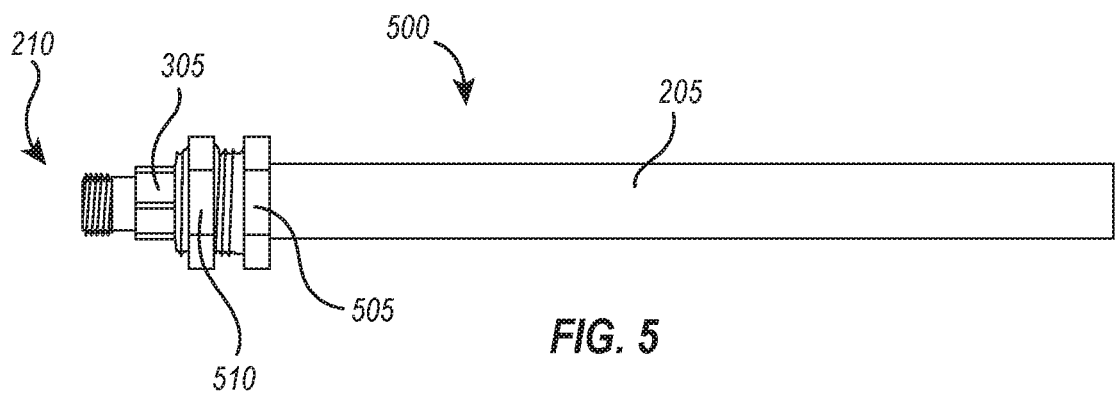
FIG. 5 illustrates a side view of a single port riser for use with a med-gas panel connector system, according to an embodiment of the present disclosure.

FIG. 5 illustrates an embodiment of a single port riser 500 that includes a manifold inlet pipe 205 and a single outlet 210. The single port riser 500 includes an inlet pipe 205 to which the outlet 210 is directly connected via a riser 505 and a lock-nut 510. The outlet 210 can also include a DISS adapter 305 similar to the outlets 210 of the other embodiments described herein.

Figure 6:
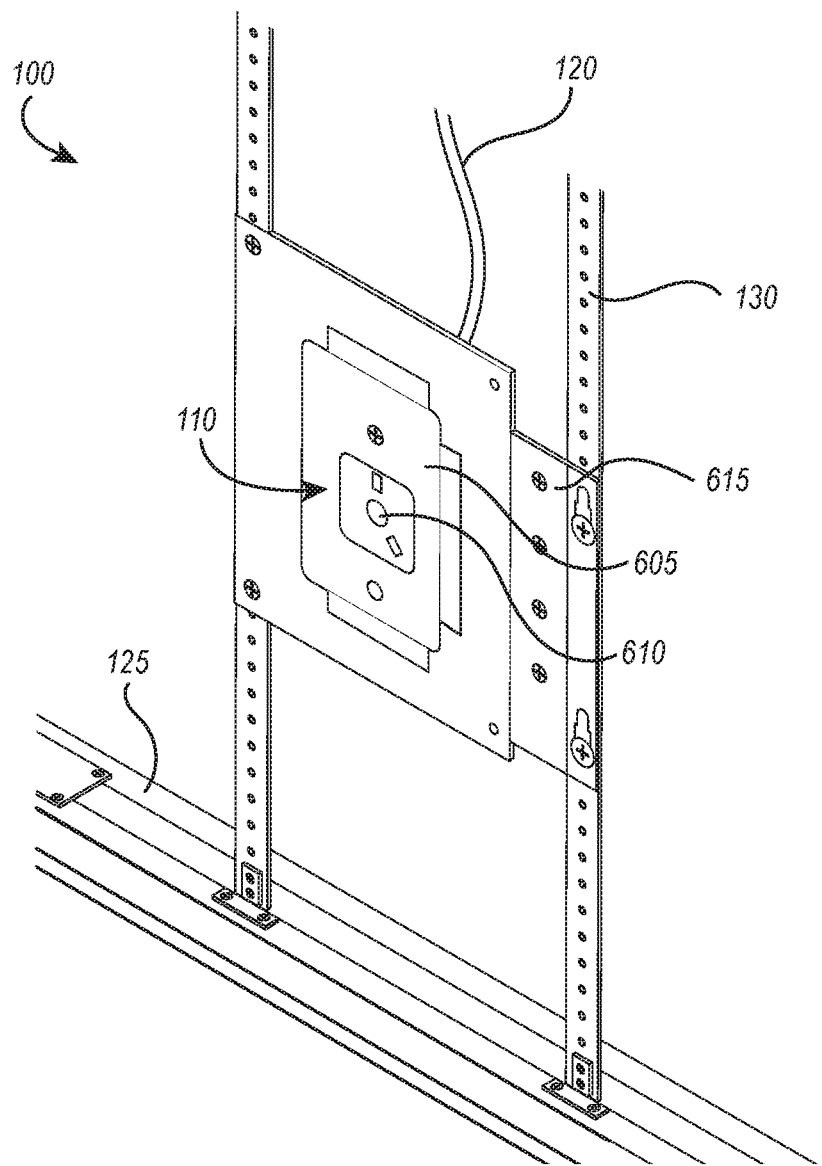
FIG. 6 illustrates a med-gas outlet for use in a med-gas panel connector system, according to an embodiment of the present disclosure.

Turning now to the med-gas outlets 110, FIG. 6 illustrates an embodiment of a med-gas outlet 110 that includes a panel 605 and a latch valve assembly 610. The latch valve assembly 610 is available in various industry standard styles that are compatible with gas valves that are inserted to access and regulate the gasses or vacuum for hoses or medical devices. A gas line 120 may be connected to an inlet on the back side of the med-gas outlet 110 to carry gas from a manifold 115 to the med-gas outlet 110. In at least one embodiment, the inlet to which the gas line 120 is connected on the back side of the med-gas outlet 110 includes a check valve and a DISS adapter and/or NIST threaded portion similar to those included with the manifold outlets 210 described herein. In at least one embodiment, the latch valve assembly 610 also includes a demand valve.

As noted above, the med-gas panel connector systems 100 of the present disclosure include one or more vertical frame members 130 and one or more horizontal frame members 125. In at least one embodiment, the med-gas outlet 110 is secured to the various frame members 125, 130 of the modular wall system 10 using one or more brackets 615. In at least one embodiment, the med-gas outlet 110 is secured to the bracket 615 and the bracket 615 is secured to one or more vertical frame members 130.

FIG. 6 illustrates an embodiment of a bracket 615 that secures the med-gas outlet 110 to two vertical frame members 130. In at least one embodiment, the bracket 615 includes a number of through-holes. In such an embodiment, the bracket 615 is secured to the vertical frame members 130 via bolts passing through the through-holes of the bracket 615 and through-holes of the vertical frame member 130. Additionally, or alternatively, in at least one embodiment, one or more outlets 110 may be secured to one or more horizontal frame members 125.

In the illustrated embodiment of FIG. 6, the position of the med-gas outlet 110 may be adjusted by securing the bracket 615 using any of the through-holes of the vertical frame member 130. In the illustrated embodiment of FIG. 6, a single med-gas outlet 110 is secured to frame members 125, 130 by a single bracket 615. In at least one embodiment, the bracket 615 may secure multiple outlets 110 to the frame members 125, 130. In this way, multiple outlets 110 may be ganged together.

For example, in at least one embodiment, two or more med-gas outlets 110 may be disposed on the bracket 615 side-by side in a horizontal configuration. In at least one embodiment, two or more med-gas outlets 110 may be disposed on the bracket 615 vertically above and below one another. In at least one embodiment, three or more med-gas outlets 110 can be ganged together in a combination of horizontal and vertical configurations as described above on a single bracket 615. In any case, the bracket 615 secures the one or more med-gas outlets 110 to the frame members 125, 135 within the med-gas panel connector systems 100 described herein.

In addition, the vertical frame members 130 may be secured anywhere along the one or more horizontal frame members 125 of the med-gas panel connector system 100. Additionally, or alternatively, the med-gas outlet 110 may be adjusted along frame members 125, 130 that do not include through-holes. In such an embodiment, a clip, clamp, or other removable securement means may secure the med-gas outlet 110 to the frame members 125, 130 such that the med-gas outlet 110 can be repositioned along the length of any of the frame members 125, 130.

Thus, the brackets 615 and frame members 125, 130 of the present disclosure provide design flexibility so that a manufacturer can position the med-gas outlets 110 at various locations within a med-gas panel connector system 100 by varying the positions of the vertical frame members 130 and horizontal frame members 125. Additionally, or alternatively, the med-gas outlets 110 may be repositioned by moving the bracket 615 relative to the frame members 125, 130.

For example, referring to FIG. 1, an assembler or installer can add, remove, or rearrange any number of vertical and horizontal frame members 130, 125 to achieve any number of desired manifold 115 and med-gas outlet 110 positions. FIGS. 1 and 6 show exemplary med-gas outlet 110 positions, but an installer and/or assembler can rearrange the frame members 125, 130, med-gas outlets 110, gas lines 120, and manifolds 115 to achieve any number of configurations. For example, an installer or assembler can form a system that includes only one or two med-gas outlets 110 arranged near the bottom of the med-gas panel connector system 100. Alternatively, an installer can assemble a system that includes ten to twenty med-gas outlets 110, or even more than twenty med-gas outlets 110, which are arranged anywhere within the med-gas panel connector system 100.

Also, for example, an installer and/or assembler can include any number of vertical and/or horizontal frame members 130, 125 in an upper portion of the med-gas panel connector system 100 so that numerous med-gas panels 110 may be secured to the upper portion of the med-gas panel connector system 100. Additionally, or alternatively, in at least one embodiment, the manifolds 115 may be disposed at the bottom of the med-gas panel connector system 100 if needed to connect to central gas lines within the floor of a hospital or other healthcare facility. In such an embodiment, the inlet pipe 205 of the manifold 115 may extend out the bottom of the med-gas panel connector system 100 through one or more horizontal frame members 125.

Also, while FIG. 1 illustrates a system that includes three manifolds 115, an assembler or installer can assemble a system that includes more or less than three manifolds 115, such as four, five, six, or seven manifolds 115, whether required for configurability or local code. Again, all components and embodiments of the med-gas panel connector systems 100 described herein are compliant with NFPA 99 standards and regulations.

The present invention can be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A medical-gas panel connector system, comprising:
  a frame assembly comprising:
    a horizontal frame member;
    a vertical frame member connected to the horizontal frame member; and
    a ceiling integration assembly comprising a horizontal member;
  a medical-gas outlet removably secured to one or more of the horizontal frame member and the vertical frame member via a bracket so that the medical-gas outlet can be repositioned within the medical-gas panel connector system anywhere along the one or more of the horizontal frame member and the vertical frame member;
  a manifold removably secured to the horizontal member of the ceiling integration assembly such that the manifold is removably positioned and secured to at any of a plurality of locations along a length of at least one of the horizontal frame member and the manifold disposed at least partially inside the medical-gas panel connector system; and
  a flexible gas line connecting the manifold to the medical-gas outlet.

2. The medical-gas panel connector system of claim 1, wherein the manifold comprises:
  an inlet pipe disposed at least partially outside the medical-gas panel connector system; and
  one or more outlets disposed at least partially inside the medical-gas panel connector system.

3. The medical-gas panel connector system of claim 2, wherein the inlet pipe of the manifold is configured to be connected to a permanent central gas line of a hospital or other medical facility during use.

4. The medical-gas panel connector system of claim 3, wherein the inlet of the manifold comprises copper and is configured to be connected to the permanent central gas line during use via welding or brazing.

5. The medical-gas panel connector system of claim 2, wherein each of the one or more outlets of the manifold comprise a DISS adapter.

6. The medical-gas panel connector system of claim 5, wherein the medical-gas outlet comprises:
  an inlet disposed on an inside of the medical-gas panel connector system, the inlet comprising:
    a DISS adapter configured to correspond to the DISS adapter of at least one of the one or more manifold outlets.

7. The medical-gas panel connector system of claim 2, wherein each of the one or more outlets of the manifold comprise an NIST threaded portion.

8. The medical-gas panel connector system of claim 1, wherein the horizontal frame member comprises a hole through which the gas line is routed between the manifold and the medical-gas outlet.

9. The medical-gas panel connector system of claim 1, wherein the vertical frame member comprises a hole through which the gas line is routed out of the medical-gas panel connector system and into an adjacent medical-gas panel connector system or panel of a modular wall system.

10. A reconfigurable wall system, comprising:
  two or more panels, the two or more panels including:
    a frame;
    a medical-gas panel connector system comprising:
      a medical-gas outlet having an inlet and a latch valve assembly;
      a manifold having an inlet and an outlet, the manifold secured to the frame such that the manifold is configured to be positioned and secured at any of a plurality of locations along a length of the frame; and a gas line connecting the outlet of the manifold to the inlet of the medical-gas outlet, wherein the medical-gas outlet is removably secured to one or more elongate frame members of the medical-gas panel connector system so that the medical-gas outlet can be repositioned within the medical-gas panel connector system anywhere along the one or more elongate frame members.

11. The reconfigurable wall system of claim 10, wherein:
the inlet of the manifold extends above the reconfigurable wall system and into a ceiling plenum of a hospital or other medical facility during use; and
the inlet of the manifold is configured to connect to a central gas line of the hospital or other medical facility during use.

12. The reconfigurable wall system of claim 11, wherein the inlet of the manifold comprises a copper pipe.

13. The reconfigurable wall system of claim 10, wherein the gas line comprises two or more gas lines, the two or more gas lines comprising:
a first gas line connecting the outlet of the manifold to the inlet of the medical-gas outlet; and
a second gas line extending out of a medical-panel connector system and into an adjacent medical-gas panel connector system or other panel of the two or more panels of the reconfigurable wall system.

14. The reconfigurable wall system of claim 10, wherein the outlet of the manifold comprises a demand valve.

15. The reconfigurable wall system of claim 10, wherein:
The inlet of the medical-gas outlet comprises a first DISS adapter;
the manifold outlet comprises a second DISS adapter; and
the first DISS adapter and the second DISS adapter correspond to one another so that the gas line connecting the outlet of the manifold to the inlet of the medical-gas outlet can only be connected to the first DISS adapter at one end and to the second DISS adapter at the other end.

16. The reconfigurable wall system of claim 10, wherein:
the medical-gas outlet comprises an inlet having a first NIST threaded portion; and
the manifold outlet comprises a second NIST threaded portion.

17. A medical-gas panel connector system, comprising:
a ceiling integration assembly;
a first manifold comprising:
an inlet extending through the ceiling integration assembly; and
an outlet comprising a DISS adapter;
a first medical-gas outlet having an inlet; and
a gas line connecting the inlet of the first medical-gas outlet to the outlet of the first manifold, wherein
the manifold is slidably and removably secured to the ceiling integration assembly so that the manifold can be secured anywhere along a length of the ceiling integration assembly, and
wherein the medical-gas outlet is removably secured to one or more elongate frame members of the medical-gas panel connector system so that the medical-gas outlet can be repositioned within the medical-gas panel connector system anywhere along the one or more elongate frame members.

18. The medical-gas panel connector system of claim 17, wherein the DISS adapter of the inlet of the first medical-gas outlet corresponds to the DISS adapter of the outlet of the first manifold so that the gas line can only connect the outlet of the first manifold to the inlet of the first medical-gas outlet.

\* \* \* \* \*